(12) United States Patent
Wang et al.

(10) Patent No.: US 8,318,794 B2
(45) Date of Patent: Nov. 27, 2012

(54) METHOD OF USE OF PORPHYRINS IN PREPARING A MEDICAMENT FOR SONODYNAMIC THERAPY AND A METHOD OF SONODYNAMIC THERAPY USING PORPHYRINS

(75) Inventors: Xiaohuai Wang, Guangzhou (CN); Jiangan Su, Shanghai (CN); Qing Li, Guangzhou (CN); Guanglian Zhao, Shanghai (CN); Yifan Luo, Guangdong Province (CN); Bo Yu, Shanghai (CN)

(73) Assignee: Science Group Pty. Ltd. (AU)

( * ) Notice: Subject to any disclaimer, the term of this patent is extended or adjusted under 35 U.S.C. 154(b) by 828 days.

(21) Appl. No.: 12/323,174

(22) Filed: Nov. 25, 2008

(65) Prior Publication Data

US 2010/0130908 A1 May 27, 2010

(51) Int. Cl.
- *A01N 43/36* (2006.01)
- *A61K 31/40* (2006.01)
- *C07B 47/00* (2006.01)
- *C07D 487/22* (2006.01)

(52) U.S. Cl. ........................... 514/427; 540/145

(58) Field of Classification Search .................. 514/427; 540/145

See application file for complete search history.

(56) References Cited

U.S. PATENT DOCUMENTS

| 4,675,338 | A | * | 6/1987 | Bommer et al. | 514/410 |
| 2004/0171601 | A1 | * | 9/2004 | Fukumura et al. | 514/185 |
| 2008/0006714 | A1 | * | 1/2008 | McNichols et al. | 239/102.2 |

FOREIGN PATENT DOCUMENTS

| CN | 1260347 A | 7/2000 |
| CN | 101156848 A | 4/2008 |
| WO | WO 2009040411 A1 * | 4/2009 |

OTHER PUBLICATIONS

Chabner et. al., Nature Rev. Cancer, 2005, Nature Publishing Group, vol. 5, pp. 65-72.*
Beger et. al., World J. Surg., 2003, Societe Internationale de Chirurgie, vol. 27, pp. 1075-1083.*
Rich et. al., Nature Rev. Drug Disc., 2004, Nature Publishing Group, vol. 3, pp. 430-446.*
Dougherty, T. J., et al., "Review—Photodynamic Therapy, 90(12)", *Journal of the National Cancer Institute*, 90(12), (Jun. 17, 1998), 889-905.
Hopper, C., et al., "mTHPC-Mediated Photodynamic Therapy for Early Oral Squamous Cell Carcinoma", *Int. J. Cancer*, 111(1) 2004, 138-146.
Jin, Zhao-Hui, et al., "Combination Effect of Photodynamic and Sonodynamic Therapy on Experimental Skin Squamous Cell Carcinoma in C3H/HeN Mice", *The Journal of Dermatology*, 27, (2000), 294-306.
Kato, H., et al., "Phase II clinical study of photodynamic therapy using mono-L-aspartyl chlorin e6 and diode laser for early superficial squamous cell carcinoma of the lung", *Lung Cancer*, 42, (2003), 103-111.
Kuroki, M., et al., "Sonodynamic Therapy of Cancer Using Novel Sonosensitizers", *Anticancer Research*, 27, (2007), 3673-3678.
Li, J., "Photodynamic Therapy and Treatment for Cancer", *Chinese Journal of Biomedical Engineering*, 24(2), (2005), 237-239.
Liu, H., et al., "Comparison of Eleven Photosensitizers' Photocytotoxicity under Irradiation of Copper Vapor Laser", *Chin. J. Laser Med. Surg.*, 11(2), (May 2002), 88-92.
Mang, T. S., et al., "A Phase II/III Clinical Study of Tin Ethyl Etiopurpurin (Purlytin)—Induced Photodynamic Therapy for the Treatment of Recurrent Cutaneous Metastatic Breast Cancer", *Cancer J. Sci. Am.*, 4(6), (1998), 378-384.
Moan, J., et al., "The photodegradation of porphyrins in cells can be used to estimate the lifetime of singlet oxygen", *Photochem. Photobiol.*, 53(4), (Abstract Only), (1991), 1 pg.
Musser, D. A., et al., "The binding of tumor localizing porphyrins to a fibrin matrix and their effects following photoirradiation", *Res. Commun. Chem. Pathol. Pharmacol.*, 28(3), (1980), 505-525.
Rosenthal, I., et al., "Sonodynamic therapy—a review of the synergistic effects of drugs and utrasound", *Ultrasonics Sonochemistry*, 11, (2004), 349-363.
Umemura, K., et al., "Sonodynamically induced antitumor effect of pheophorbide a", *Cancer Letters*, 102, (1996), 151-157.
Yao, J. Z., et al., *Chinese Journal of Pharmaceuticals*, 31(5), (2000), 215-217.
Yumita, N., et al., "Sonodynamically-induced apoptosis, necrosis, and active oxygen generation by mono-l-aspartyl chlorin ef", *Cancer Sci.*, 99(1), (2008), 166-172.

* cited by examiner

*Primary Examiner* — Sreeni Padmanabhan
*Assistant Examiner* — Sarah Pihonak
(74) *Attorney, Agent, or Firm* — Harness, Dickey & Pierce, P.L.C.

(57) ABSTRACT

The invention provides method of use of a porphyrin compound as shown below in preparing a medicament for sonodynamic therapy, and a method of sonodynamic therapy using a porphyrin compound. Said therapy comprises administering a porphyrin compound to a patient and applying sonic wave to the patient, -continued
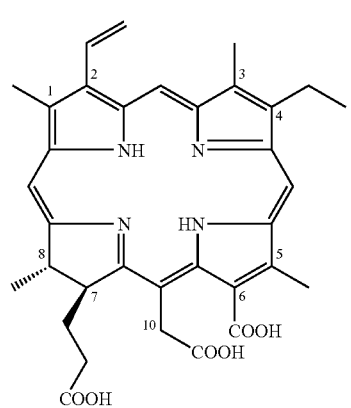
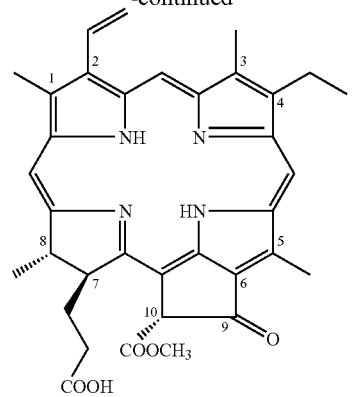
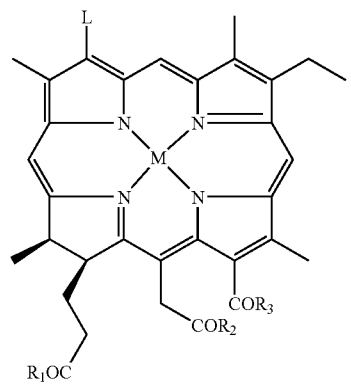
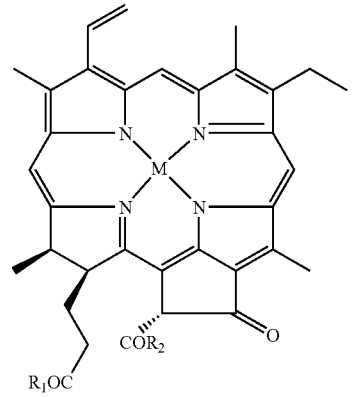
wherein each symbol has the meaning as defined in the description.
6 Claims, 3 Drawing Sheets

METHOD OF USE OF PORPHYRINS IN PREPARING A MEDICAMENT FOR SONODYNAMIC THERAPY AND A METHOD OF SONODYNAMIC THERAPY USING PORPHYRINS

FIELD OF THE INVENTION

The invention relates to a method of use of a porphyrin compound in preparing a medicament for sonodynamic therapy (SDT) and a method of sonodynamic therapy using a porphyrin compound.

BACKGROUND OF THE INVENTION

Malignant tumors are a leading cause of death in modern societies. Photodynamic therapy (PDT) has been used for more than 100 years to treat tumors, and sonodynamic therapy has been very recently developed. With appropriate sensitizers, both have high efficacy, high selectivity and low side effects. There are good prospects of their wide clinical application (see Li Jian et al., Chinese Journal of Biomedical Engineering. 2005, 24:237-239; Thomas J., et al, Journal of the National Cancer Institute, 1998, 90: 889-905; Ionel Rosenthal et al, Ultrasonics Sonochemistry, 2004, 11: 349-336).

PDT is carried out in two steps: initially injecting or administering orally a photosensitive agent to a patient, and then activating the photosensitive agent by exposing the patient to light at an appropriate wavelength to produce "singlet oxygen", thereby killing abnormal cells and microorganisms (see Moan J. et al, Photochem. Photobiol. 1991; 53: 549-553). Since the photosensitive agent administered is specifically concentrated in abnormal cells, such as cancer cells, the therapy is effective in destroying these cells with minimal damage to normal cells (see Thomas J., et al, Journal of the National Cancer Institute, 1998, 90: 889-905; Musser D. A. et al, Res. Commun. Chem. Pathol. Pharmacol. 1980; 28:505-525). It is particularly effective in treating early-stage and superficial tumors, with an efficacy of 84-100% [Hopper C. et al. Int. J Cancer. 2004, 111(1):138-146; Kato H. et al. Lung Cancer. 2003, 42:103-111; Mang T. S. et al. Cancer J Sci. Am.; 1998, 4:378-84].

PDT, however, has three main disadvantages. Firstly, since the red light, usually used therein, penetrates the human body only to a depth of up to 10 mm, PDT is only used to treat tumors occurring in very superficial or topical areas (see Thomas J., et al, Journal of the National Cancer Institute, 1998, 90: 889-905). Secondly, since the currently available photosensitive agents are metabolized at a low speed in normal cells, after treatment, patients must be protected from light for a period of 30 days, to prevent photosensitive dermatitis (see Li Jian, Chinese Journal of Biomedical Engineering, 2005, 24:237-239). Thirdly, PDT typically requires an interventional procedure to introduce optical fibers into the body or tumor, thus increasing pain and risk for patients (see Kato H. et al, Lung Cancer. 2003, 42(1):103-111).

Sonodynamic therapy has been developed as a therapy complementary or alternative to PDT. It treats cancers with ultrasound and sound-sensitive agents (see Joe Z., et al., Ultrasonics Sonochemistry, 2004, 11: 349-336). The mechanism is that the ultrasounds activate the sound-sensitive agent in body to produce singlet oxygen, thus killing abnormal cells such as tumor cells (see Kuroki M. et al,. 2007, Anticancer Res. 27:3673-3677). A synergistic effect may be observed if SDT is combined with chemotherapy or PDT (see Jin Z H et al, J Dermatol, 2000, 27: 294-306; Ionel Rosenthal et al., Ultrasonics Sonochemistry, 2004, 11: 349-336). Clinical applications of SDT, however, have not been reported, not least because no suitable sound-sensitive agents are available that are both specifically enriched in focal areas and sufficiently high sound-sensitive to produce singlet oxygen, which kills abnormal cells such as tumor cells.

Porphyrin compounds have been known to serve as photo-sensitive and sound-sensitive agents. They selectively adhere to abnormal cells such as tumor cells (see Yao J Z et al., Chin J Pharmaceuticals 2000; 31: 2157; Liu H L et al., Chin J Laser Med Surg 2002; 11: 889; Umemura K et al., Cancer Lett., 1996, 102: 151-157; Yumita N et al., Cancer Science, 2008, 99: 166-172). In the case of SDT, however, no satisfactory sound-sensitive agents and thus suitable therapies are available for clinical application at present.

SUMMARY OF THE INVENTION

The invention provides a method of use of a porphyrin compound in preparing a medicament for sonodynamic therapy, said therapy comprising administering a porphyrin compound to a patient and applying sonic wave to the patient.

The invention also provides a method of sonodynamic therapy, comprising administering a porphyrin compound to a patient and applying sonic wave to the patient.

The porphyrin compounds used in the invention are porphyrin compounds and chlorophyllin compounds having a structural formula shown below:

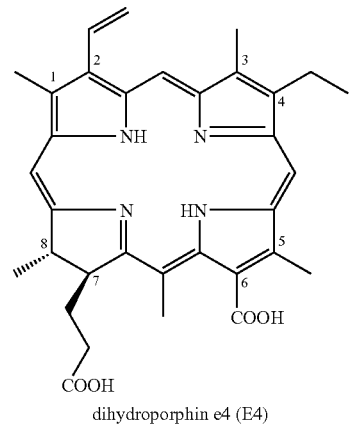

dihydroporphin e4 (E4)

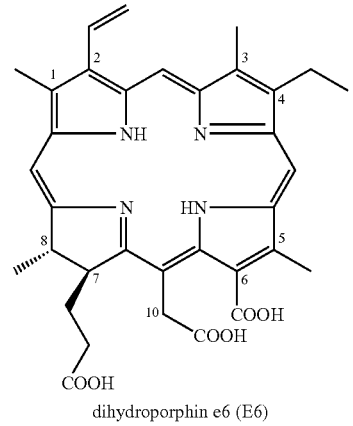

dihydroporphin e6 (E6)

-continued

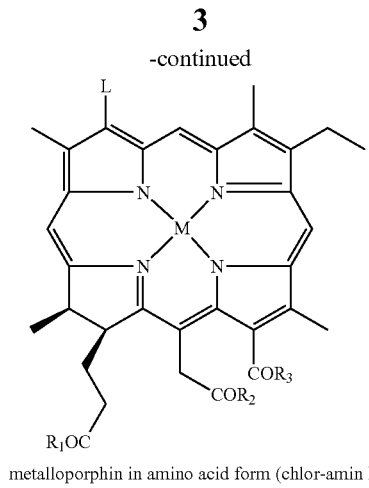

metalloporphin in amino acid form (chlor-amin M)

wherein, M represents $Zn^{2+}$, $Sn^{2+}$, $Sn^{4+}$, $Fe^{2+}$, $Cu^{2+}$, $Mg^{2+}$, $Ni^{2+}$ or $Co^{2+}$, L represents $CH=CH_2$ or

$R_1$ represents OH, $OCH_3$ or a residue of an amino acid, $R_2$ represents OH or a residue of an amino acid, $R_3$ represents OH or a residue of an amino acid, and wherein said amino acid is selected from the group consisting of glycine, alanine, valine, leucine, isoleucine, phenylalanine, proline, tryptophane, tyrosine, serine, cysteine, methionine, asparagine, glutamine, threonine, aspartic acid, glutamic acid, lysine, arginine and histidine; if $R_1$ or $R_2$ represents a residue of an amino acid, the N end of the amino acid represented by $R_1$ or $R_2$ is directly linked with the C atom literally indicated in the formula; if there are two or more N ends in the amino acid represented by $R_1$ or $R_2$, one of these N ends is directly linked with the C atom literally indicated in the formula;

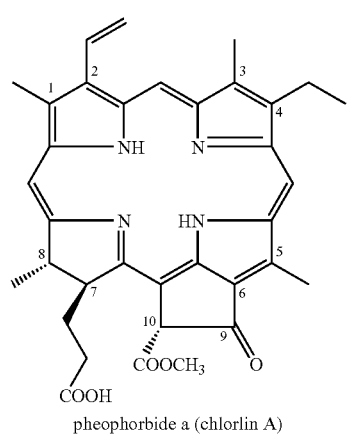

pheophorbide a (chlorlin A)

-continued

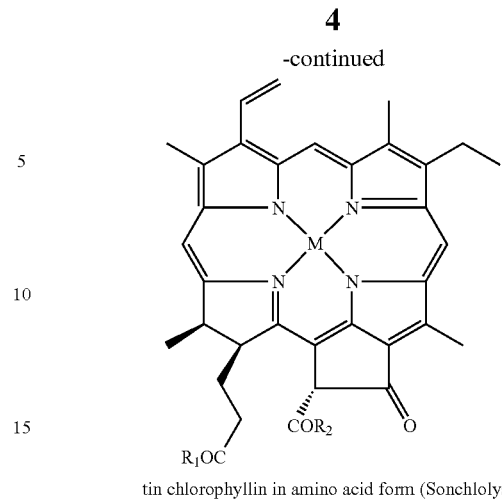

tin chlorophyllin in amino acid form (Sonchlolyse)

wherein, M represents $Sn^{2+}$ or $Sn^{4+}$; $R_1$ represents OH or a residue of an amino acid; $R_2$ represents OH or a residue of an amino acid; and wherein said amino acid is selected from the group consisting of glycine, alanine, valine, leucine, isoleucine, phenylalanine, proline, tryptophane, tyrosine, serine, cysteine, methionine, asparagine, glutamine, threonine, aspartic acid, glutamic acid, lysine, arginine and histidine; if $R_1$ or $R_2$ represents a residue of an amino acid, the N end of the amino acid represented by $R_1$ or $R_2$ is directly linked with the C atom literally indicated in the formula; if there are two or more N ends in the amino acid represented by $R_1$ or $R_2$, one of these N ends is directly linked with the C atom literally indicated in the formula.

DETAILED DESCRIPTION OF THE INVENTION

Figure 1:
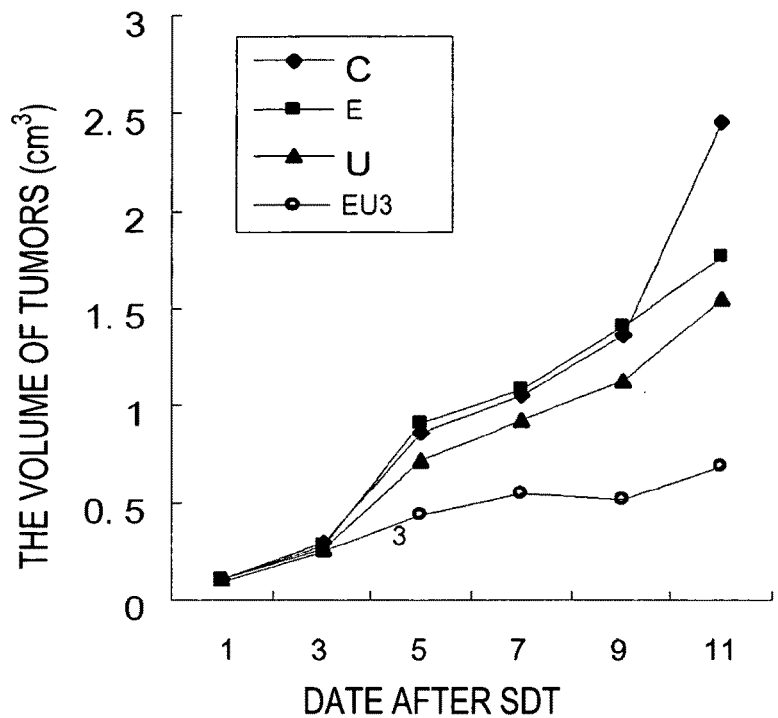
FIG. 1 represents a diagram showing a tumor developing profile observed in the SDT group administered with dihydroporphin e4, compared to three control groups in animal tests.

The invention provides method of use of one of the porphyrin compounds as shown below in preparing a medicament for sonodynamic therapy, said therapy comprising administering the porphyrin compound to a patient and applying sonic wave to the body of the patient.

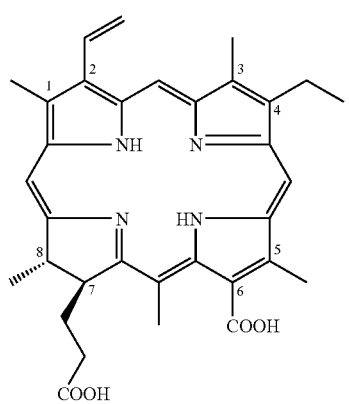

dihydroporphin e4 (E4)

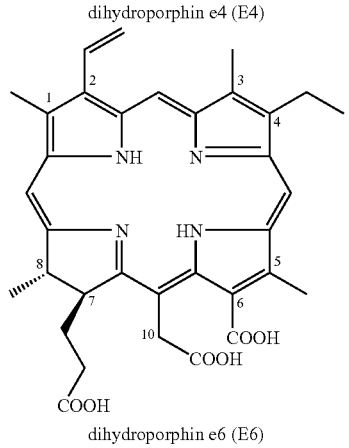

dihydroporphin e6 (E6)

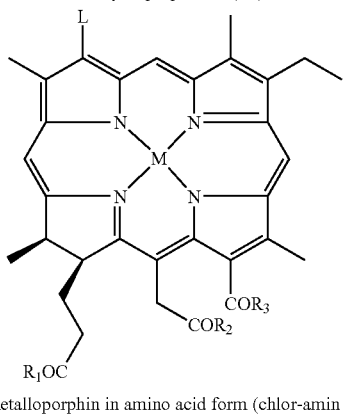

metalloporphin in amino acid form (chlor-amin M)

wherein, M represents $Zn^{2+}$, $Sn^{2+}$, $Sn^{4+}$, $Fe^{2+}$, $Cu^{2+}$, $Mg^{2+}$, $Ni^{2+}$ or $Co^{2+}$, L represents $CH=CH_2$ or

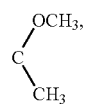

$R_1$ represents OH, $OCH_3$ or a residue of an amino acid, $R_2$ represents OH or a residue of an amino acid, $R_3$ represents OH or a residue of an amino acid, and wherein said amino acid is selected from the group consisting of glycine, alanine, valine, leucine, isoleucine, phenylalanine, proline, tryptophane, tyrosine, serine, cysteine, methionine, asparagine, glutamine, threonine, aspartic acid, glutamic acid, lysine, arginine and histidine; if $R_1$ or $R_2$ represents a residue of an amino acid, the N end of the amino acid represented by $R_1$ or $R_2$ is directly linked with the C atom literally indicated in the formula; if there are two or more N ends in the amino acid represented by $R_1$ or $R_2$, one of these N ends is directly linked with the C atom literally indicated in the formula.

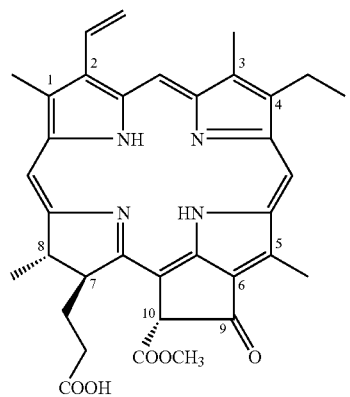

pheophorbide a (chlorlin A)

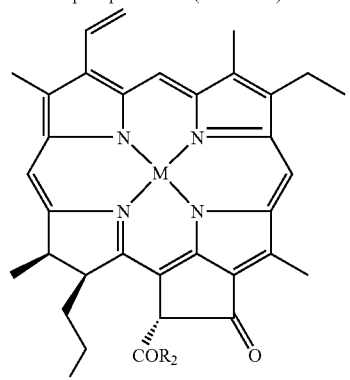

tin chlorophyllin in amino acid form (Sonchlolyse)

wherein, M represents $Sn^{2+}$ or $Sn^{4+}$; R1 represents OH or a residue of an amino acid; R2 represents OH or a residue of an amino acid; and wherein said amino acid is selected from the group consisting of glycine, alanine, valine, leucine, isoleucine, phenylalanine, proline, tryptophane, tyrosine, serine, cysteine, methionine, asparagine, glutamine, threonine, aspartic acid, glutamic acid, lysine, arginine and histidine; if $R_1$ or $R_2$ represents a residue of an amino acid, the N end of the amino acid represented by $R_1$ or $R_2$ is directly linked with the C atom literally indicated in the formula; if there are two or more N ends in the amino acid represented by $R_1$ or $R_2$, one of these N ends is directly linked with the C atom literally indicated in the formula.

Animal tests demonstrate that the porphyrin compounds used according to the invention are highly concentrated in focal tissues, while occurring at low concentrations in normal tissues. This enables SDT to be used in clinical treatment. Here, it is to be understood that, while the term "human body" is usually referred to in illustration and explanation of the invention, the invention also applies to other mammals, as would be readily recognized by those skilled in the art.

In a preferred embodiment of the method of use according to the invention, the therapy comprises applying sonic wave to the body topically.

In a preferred embodiment of the method of use according to the invention, the therapy comprises applying sonic wave to the body systemically.

In a preferred embodiment of the method of use according to the invention, the sonic wave applied is ultrasound.

In a preferred embodiment of the method of use according to the invention, the ultrasound applied has a frequency in the range of 0.1-10 MHz, preferably 0.5-2.5 MHz.

In a preferred embodiment of the method of use according to the invention, the ultrasound applied has a power density in the range of 0.1-3.0 W/cm$^2$, preferably 0.2-2.0 W/cm$^2$, more preferably 0.3-1.2 W/cm$^2$.

In a preferred embodiment of the method of use according to the invention, the ultrasound applied has an energy density of more than 10 J/cm$^2$, preferably in the range of 60-300 J/cm$^2$, more preferably 108-212 J/cm$^2$ (energy density of ultrasound=power density (W/cm$^2$)×irradiation time (sec)=J/cm$^2$).

In a preferred embodiment of the method of use according to the invention, the sonic wave is applied to the human body via a liquid, preferably water, as transmission medium.

In a preferred embodiment of the method of use according to the invention, the SDT therapy comprises applying both sonic wave and light wave to the body of the patient, either topically or systemically, preferably systemically, the amount of light wave applied being that commonly used for this purpose in the art.

The invention also provides a method of sonodynamic therapy, comprising administering one of the porphyrin compounds as described above to a patient, and applying sonic wave to the body of the patient.

In a preferred embodiment of the method of therapy according to the invention, the therapy comprises applying sonic wave to the body of the patient topically.

In a preferred embodiment of the method of therapy according to the invention, the therapy comprises applying sonic wave to the body of the patient systemically.

In a preferred embodiment of the method of therapy according to the invention, the sonic wave applied is ultrasound.

In a preferred embodiment of the method of therapy according to the invention, the ultrasound applied has a frequency in the range of 0.1-10 MHz, preferably 0.5-2.5 MHz.

In a preferred embodiment of the method of therapy according to the invention, the ultrasound applied has a power density in the range of 0.1-3.0 W/cm$^2$, preferably 0.2-2.0 W/cm$^2$, more preferably 0.3-1.2 W/cm$^2$.

In a preferred embodiment of the method of therapy according to the invention, the ultrasound applied has an energy density of more than 10 J/cm$^2$, preferably in the range of 60-300 J/cm$^2$, more preferably 108-212 J/cm$^2$ (an energy density of ultrasound=power density (W/cm$^2$)×irradiation time (sec)=J/cm$^2$).

In a preferred embodiment of the method of therapy according to the invention, the sonic wave is applied to the body of the patient via a liquid, preferably water, as transmission medium.

In a preferred embodiment of the method of therapy according to the invention, the SDT comprises applying both sonic wave and light wave to the body of the patient, either topically or systemically, preferably systematically, the amount of light wave applied being that commonly used for this purpose in the art.

In the metalloporphins in amino acid form used according to the invention, M is preferably Zn or Sn, particularly Sn$^{4+}$. L is preferably CH=CH$_2$, $R_1$ is preferably OH, $R_2$ is preferably a residue of lysine, $R_3$ is preferably OH.

In the tin chlorophyllin in amino acid form used according to the invention, preferably, M is Sn$^{4+}$, $R_1$ is a residue of lysine, and $R_2$ is a residue of lysine.

The porphyrins compounds used in the invention are known from, e.g. Chinese patent application No. 99119878.6, published on Jul. 19, 2000 as CN1260347 (the applicant and inventor is Xu Deyu, and the title is "Metal complexes as Product of Degradation of Chlorophyll a, Their Preparation and Anti-Gastric Ulcer Medicaments Containing the Same").

As an example, pheophorbide a, dihydroporphin e4, dihydroporphin e6, and a tin chlorophyllin in lysine form are obtained by the following process:
1. dissolving a crude chlorophyll in diethyl ether, adding 36% hydrochloric acid, stirring the resultant mixture at 4° C. for 1.5 h, and allowing it to stand for 1 h to separate an acidic aqueous layer, diluting the acidic aqueous layer with water, adjusting pH to 5-6 with 10M sodium hydroxide, filtering the resultant mixture and drying the residue to obtain a solid, which is in turn separated by column chromatography on silicon gel H to give the pheophorbide a as black powder;
2. dissolving crude pheophorbide a in pyridine, adding a 25% (w/v) solution of potassium hydroxide in methanol under N$_2$, and stirring the resultant mixture under reflux for 30 min, slightly cooling the reaction mixture, adding water, and adjusting pH to 5-6 with 10% sulfuric acid, filtering the resultant mixture and drying the residue, which is then separated by column chromatography on silicon gel H to give dihydroporphin e6 as black powder;
3. dissolving dihydroporphin e6 in pyridine, stirring the resultant solution under reflux for 45 min, slightly cooling the reaction mixture and adding water, adjusting pH to 5-6 with 10% (w/v) sulfuric acid, filtrating the resultant mixture and drying the residue, which is then separated by column chromatography on silicon gel H to give dihydroporphin e4 as black powder.
4. dissolving pheophorbide a in tetrahydrofuran, adding a 2% (w/v) solution of stannous chloride in methanol, and stirring the resultant mixture under reflux in a water bath for 30 min, adding water, filtrating the resultant mixture and drying the residue, which is then separated by column chromatography on silicon gel H to give tin-containing chlorophyllin.
5. mixing the tin-containing chlorophyllin with lysine di-t-butyl ester, adding an equal volume of dicy-clohexyl carbodiimide (DCC) as condensing agent, stirring the resultant mixture at 0-4° C. for 2.0 h, to the reaction mixture adding trifluoroacetic acid, stirring at 55-60° C. for another 3.0 h, allowing the mixture to stand while cooling, which is then separated by column chromatography on silicon gel H to give the lysine form of tin chlorophyllin (Sonchlolyse).

The porphyrin compounds can be used singly or in combination. They can be formulated into suitable dosage forms, including liquid and solid formulations, such as an injection solution, an oral liquid formulation and a tablet, a sublingual tablet and gargle, a rectal suppository, and other suitable dosage forms. For this purpose, the porphyrin compounds can be used in admixture with an excipient, a preservative and the like, or be encapsulated.

According to the invention, the porphyrin compounds are used at an amount of 0.05-10 mg/kg of body weight, preferably 0.3-3 mg/kg, more preferably 0.5-1.5 mg/kg.

The sonic wave applied according to the invention can be any of those which induce the porphyrin compounds to produce "singlet oxygen". Ultrasound is preferably applied.

According to the invention, the sonic wave is preferably applied via a liquid, preferably water, as transmission medium. Thus, when being treated, the patient can be placed in contact with a liquid, preferably water, through which the sonic wave is then transmitted to the patient.

In a preferred embodiment according to the invention, the ultrasound is essentially parallel wave, scattered wave, continuous wave or discontinuous wave. It has a frequency of 0.1-10 MHz, preferably 0.5-2.5 MHz. The ultrasound has a power density in the range of 0.1-3.0 $W/cm^2$, preferably 0.2-2.0 $W/cm^2$, more preferably 0.3-1.2 $W/cm^2$; and an energy density more than 10 $J/cm^2$, preferably 60-300 $J/cm^2$, more preferably 108-212 $J/cm^2$.

In the method of therapy according to the invention, a pharmaceutical formulation containing one of the porphyrin compounds is firstly administered to a patient, and then, after 1-72 h, preferably 6-48 h, more preferably 12-36 h, even more preferably 18-24 h, sonic waves are applied to the body of the patient. The sonic wave can be applied once or more times a day, and for a time period, the sonic wave can be applied every day or every other day. The porphyrin compound, which is enriched in focal tumor tissues, is accordingly activated by the sonic wave to produce "singlet oxygen", which in turn kills abnormal cells and micro-organisms.

The porphyrin compounds used according to the invention have high specific selectivity to tumors and rapid elimination from non-tumor tissues. When at amounts that are several times the therapeutically effective amount, the compounds display substantially no toxicity to human body and thus they can ensure an optimal T/N ratio (the ratio of the content of a sound-sensitive agent in tumor cells to that in normal cells) to be achieved after administration of it. There are low side effects; thus, these compounds are therapeutically efficient and safe. Additionally, the porphyrin compounds are highly sensitive to ultrasound, as well as to light. Therefore, they afford a therapy effective to many tumor types, even effective and safe for advanced cancer patients who suffer from systemic failures. In particular, the SDT therapy according to the invention can be used in the treatment of tumors in difficult-to-treat areas, such as brain stem and spinal cord, providing an effective and safe therapeutic means.

The invention will be illustrated by the following non-limiting examples.

EXAMPLES

I. Animal Test A
1. Materials and Method
1.1 Sound-Sensitive Agent

The sound-sensitive agent, dihydroporphin e4, is prepared according to Chinese Patent No. 99119878.6. The agent is dissolved in water for injection in darkness to give a final concentration of 4 mg/mL. The resultant solution is stored at 4° C. in darkness.

1.2 Tumor Strain and Test Animals

The animal tumor model used in this study was the KM mouse S-180 sarcoma, which is one of the tumor models appointed by the China Food and Drug Administration (CFDA) for new anticancer drug testing. Mouse S-180 sarcoma cell line was commercially available from the Cancer Hospital affiliated to Sun Yat-sen University. The inbred strain of KM mice (female, about 18-20 g body weight) was bred and tested in a laboratory consistent with national standards for new drug tests (the Animal Experimental Centre of Guangzhou Chinese Traditional Medical University). The mouse S-180 sarcoma cell line was injected into and raised in the abdominal cavity of the KM mouse and regenerated 3 times by passing malignant ascites from one mouse to another to confirm their growth is stable.

1.3 Ultrasound Apparatus

The ultrasound having a frequency of 1.0 MHz and an adjustable power density in the range of 0.1-2.2 $W/cm^2$ is applied. The apparatus can emit parallel wave, continuous wave or discontinuous wave.

2. Method
2.1 Establishment of Tumor Models

The ascites with S-180 cell suspension was drawn out from the abdomen of the third passage mouse, and germ-free physiological saline solution was added. The final concentration of the cell suspension was $1\times10^7$ cells/mL. 0.1 mL of the cell suspension was injected subcutaneously in the right axilla of the mouse to grow a solid tumor.

2.2 Test Groups:

Three days later, a small mass with the average diameter of about 0.4 cm was seen and palpated on every implanted mouse axilla. These tumor-bearing mice are divided randomly into the following groups with 5 mice in each group:

1) a blank control group (C);
2) a ultrasound group (U), which are simply treated with ultrasound (having a frequency of 1.0 MHz and a power density of 1.6 $W/cm^2$) without injection of the sound-sensitive agent;
3) a sound-sensitive agent group (E), which are simply injected with the sound-sensitive agent without treatment of ultrasound;
4) a 0.4 group (EU1), which are injected with the sound-sensitive agent and subsequently treated with ultrasound having a frequency of 1.0 MHz and a power density of 0.4 $W/cm^2$;
5) a 0.8 group (EU2), which are treated according to EU1 except using ultrasound having a power density of 0.8 $W/cm^2$; and
6) a 1.6 group (EU3), which are treated according to EU1 except using ultrasound having a power density of 1.6 $W/cm^2$.

2.3 Injection of Sound-Sensitive Agent

To prepare the mice for the experiment, the fur on the tumor-bearing area of the mice was removed with depilatory cream. For the E, EU1, EU2 and EU3 groups, the sound-sensitive agent was injected into each mouse abdominal cavity in a dose of 40 mg/kg in a dark room. The mice are kept in darkness.

2.4 Ultrasound Treatment

Six hours after the injection, each mouse of the EU1, EU2 and EU3 groups and the U group is partially immerged in water with only their head remaining above the water surface. An ultrasound probe was then placed into the water to irradiate the tumor area at the above parameters for 3 minutes. The mice of each group are fed in a conventional way.

2.5 Observation of Tumor Volume and Weight

After treatment with SDT, primary tumor size were estimated by measuring perpendicular minor dimension (W) and major dimension (L) using sliding calipers every one or two days. Approximate tumor volume was calculated by the formula: $W^2L\times\frac{1}{2}$.

12 days later, the mice are sacrificed by breaking the cervical vertebrae. The tumor tissues are separated and weighed on an electronic balance to calculate an average weight. Various groups are compared in terms of their respective average tumor weight at the $12^{th}$ day.

2.6 Statistic Analysis

In comparing the tumor weights of various groups, statistic analysis is performed using the Student's t test.

3. Results 3.1 The SDT Therapy with Dihydroporphin e4 Inhibits the Growth of the S-180 Tumors in the Mice.

As shown in FIG. 1, there was a gradually rapid increase in the average tumor volume of each control group (C, U and E) since the test began. The E and U groups displayed a slower increase compared with the blank control group. The comparison of the tumor weights at the $12^{th}$ day (see Table 1) shows that there are significant differences ($p<0.05$) between the E and C groups or between the E and C groups, implying a possible inhibiting effect of ultrasound or dihydroporphin e4 alone on the S-180 tumor. An even slower tumor development occurred in the EU3 group after the SDT treatment (see FIG. 1). There is a very significant difference ($p<0.01$) of the tumor weight data between the EU3 group and the C, U or E group (see Table 1) at the end of the test. The synergistic effect is obviously present between dihydroporphin e4 and ultrasound, which significantly inhibits the growth of the S-180 tumors in mice.

TABLE 1

Comparison of Tumor Weight between SDT Group Administered with Dihydroporphin e4 and Three Control Groups, 12 Days after Treatment

| Groups | Average Tumor Weights (g) | P (compared with C) | P (compared with U) | P (compared with E) |
|---|---|---|---|---|
| C | 3.2200 ± 0.1483 | | <0.05 | <0.05 |
| U | 1.8400 ± 0.3435 | <0.05 | | >0.05 |
| E | 1.8800 ± 0.3114 | <0.05 | >0.05 | |
| EU3 | 0.5200 ± 0.0837 | <0.01 | <0.01 | <0.01 |

3.2 The Therapeutic Effect of the SDT Therapy with Dihydroporphin e4 Depends on the Power Density of Ultrasound.

Figure 2:
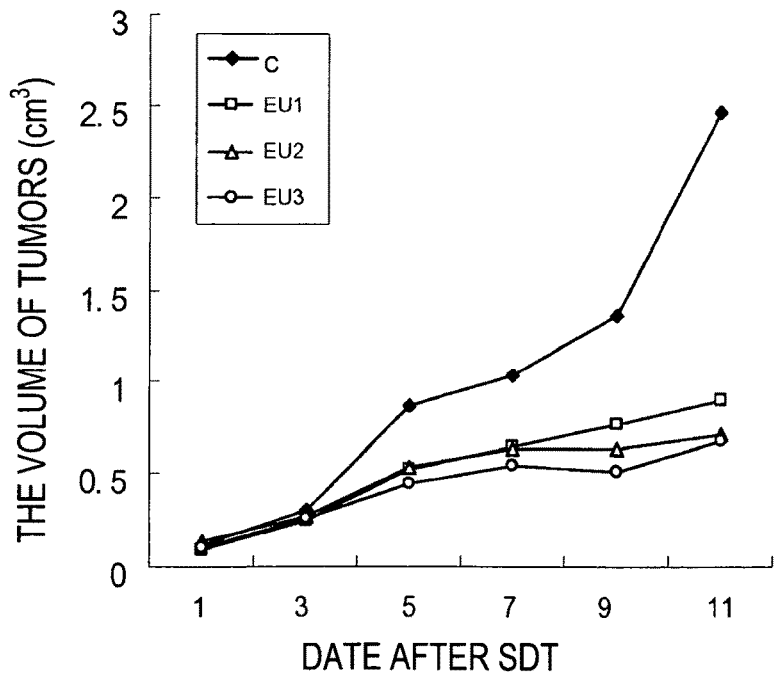
FIG. 2 represents a diagram showing tumor developing profiles observed in three SDT groups administered with dihydroporphin e4, compared to a control group in animal tests.

FIG. 2 and Table 2 show the results of the study on the relationship between the therapeutic effect of the SDT and the power density of ultrasound. As can be seen in FIG. 2, the tumor growth is significantly inhibited by the SDT therapy with dihydroporphin e4 when ultrasound having a power density in the range of 0.4 W/cm$^2$-1.6 W/cm$^2$ is applied. The therapeutic effect increases proportionally to the power density.

12 days later, the tumor tissues were excised and weighed (see Table 2). Compared with the control group, the EU1, EU2, and EU3 groups had the significantly lower average tumor weights with a very significant difference ($P<0.01$). Additionally, the EU1 group had the average tumor weight with a very significant difference ($P<0.01$) compared with the EU3 group. This demonstrates that the therapeutic effect of the SDT therapy with dihydroporphin e4 depends on the power density of ultrasound, and thus further confirms that the therapeutic effect of the SDT therapy depends on the synergistic effect of dihydroporphin e4 and ultrasound. The SDT therapy with dihydroporphin e4 can indeed inhibit the growth of the S-180 tumors in mice.

TABLE 2

Comparison of Tumor Weights between Three SDT Groups Administered with Dihydroporphin e4 and Control Group, 12 Days after Treatment

| Groups | Average Tumor Weights (g) | P (compared with C) | P (compared with EU3) |
|---|---|---|---|
| C | 3.2200 ± 0.1483 | | <0.01 |
| EU1 | 0.7600 ± 0.0894 | <0.01 | <0.01 |
| EU2 | 0.5800 ± 0.0837 | <0.01 | >0.05 |
| EU3 | 0.5200 ± 0.0837 | <0.01 | |

II. Animal Test B

1. Materials and Method 1.1 Sound-Sensitive Agent

The sound-sensitive agent was the amino acid form of tin chlorophyllin, wherein M is Sn$^{4+}$, $R_1$ is a residue of lysine, and $R_2$ is a residue of lysine; the agent was obtained according to the previous process. The agent was dissolved in 0.1 mol/L phosphate buffer (pH 7.2-7.4) in darkness to give a final concentration of 2 mg/mL. The resultant solution was stored at 4° C. in a dark and quiet place.

1.2 Tumor Strain and Test Animals

The same as used in the above Animal Test A.

1.3 Ultrasound Apparatus

The same as used in the above Animal Test A.

2. Method 2.1 Establishment of Tumor Models

The same as established in the above Animal Test A.

2.2 Test Groups:

After four days, touchable tumors with the average diameter of about 0.6 cm are developed subcutaneously at the right axillae of the mice. These tumor-bearing mice are divided randomly into the following groups:

1) a blank control group (C);
2) a ultrasound group (U), which are simply treated with ultrasound (having a frequency of 1.0 MHz and a power density of 1.2 W/cm$^2$) without injection of the sound-sensitive agent;
3) a sound-sensitive agent group (S), which are simply injected with the sound-sensitive agent without treatment of ultrasound;
4) a 0.3 group (SU1), which are injected with the sound-sensitive agent and subsequently treated with ultrasound having a frequency of 1.0 MHz and a power density of 0.3 W/cm$^2$;
5) a 0.6 group (SU2), which are treated according to SU1 except using ultrasound having a power density of 0.6 W/cm$^2$; and
6) a 1.2 group (SU3), which are treated according to SU1 except using ultrasound having a power density of 1.2 W/cm$^2$.

2.3 Injection of Sound-Sensitive Agent

A depilatory cream is applied to remove fur on the areas to be irradiated. For the S, SU1, SU2 and SU3 groups, the sound-sensitive agent is injected intraperitoneally to each mouse at a dose of 20 mg/kg in a dark room. The mice are then fed in darkness.

2.4 Ultrasound Treatment 6 h after injection, each mouse of the SU1, SU2 and SU3 groups and the U group is partially immersed in water with only their head remaining above the water surface. An ultrasond probe was then placed into the water to irradiate the tumor area at the above parameters for 180 seconds. The mice of each group are fed in a conventional way.

2.5 Observation of Tumor Volume and Weight

The same as in the above Animal Test A.

15 days later, the mice are sacrificed by breaking the cervical vertebrae. The tumor tissues are separated and weighed on an electronic balance to calculate an average weight. Various groups are compared in terms of their respective average tumor weights at the $15^{th}$ day.

2.6 Statistic Analysis

The same as in the above Animal Test A.

3. Results 3.1 The SDT Therapy with the Lysine Form of Tin Chlorophyllin Inhibits the Growth of the S-180 Tumors in the Mice.

Figure 3:
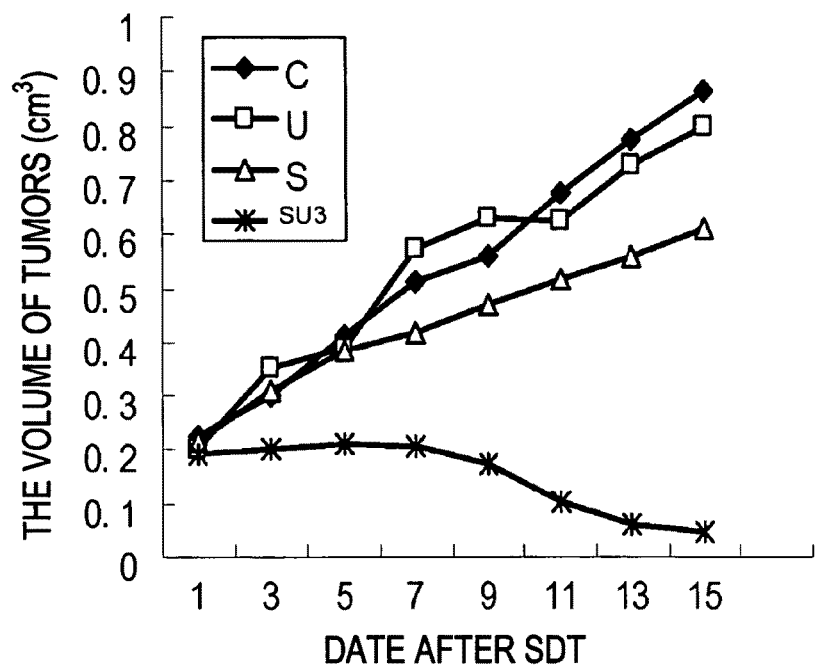
FIG. 3 represents a diagram showing a tumor developing profile observed in the SDT group administered with the lysine form of tin chlorophyllin, compared to three control groups in animal tests.

As can be seen in FIG. 3, there was a gradual increase in the average tumor volume of each control group (C, U and S) since the test began. The U and S groups displayed a slower increase compared to the blank control group. The comparison of the tumor weights at the 15$^{th}$ day (see Table 3) shows that no significant difference is present between the U, and S groups, on the one hand, and the blank control group, on the other (p>0.05). For the SU3 group, the average tumor volume hardly increased during the first six days after the SDT treatment, and began to decrease from the 7$^{th}$ day, and noticeably lower at the 15$^{th}$ day than before the test (see FIG. 3). There is a very significant difference (p<0.01) of the tumor weight data between the SU3 group and the C, U or S group (see Table 3) at the end of the test. Obviously, the SDT therapy with the lysine form of tin chlorophyllin can indeed inhibit the growth of the S-180 tumors in mice.

TABLE 3

Comparison of Tumor Weight between SDT Group Administered with Lysine Form of Tin Chlorophyllin and Three Control Groups, 15 Days after Treatment

| Group | Average Tumor Weight (g) | P (compared to C) |
|---|---|---|
| C | 0.362 ± 0.096 | |
| U | 0.334 ± 0.285 | >0.05 |
| S | 0.269 ± 0.331 | >0.05 |
| SU3 | 0.011 ± 0.004 | <0.01 |

3.2 The Therapeutic Effect of the SDT Therapy with the Lysine Form of Tin Chlorophyllin Depends on the Strength of the Power Density of Ultrasound.

Figure 4:
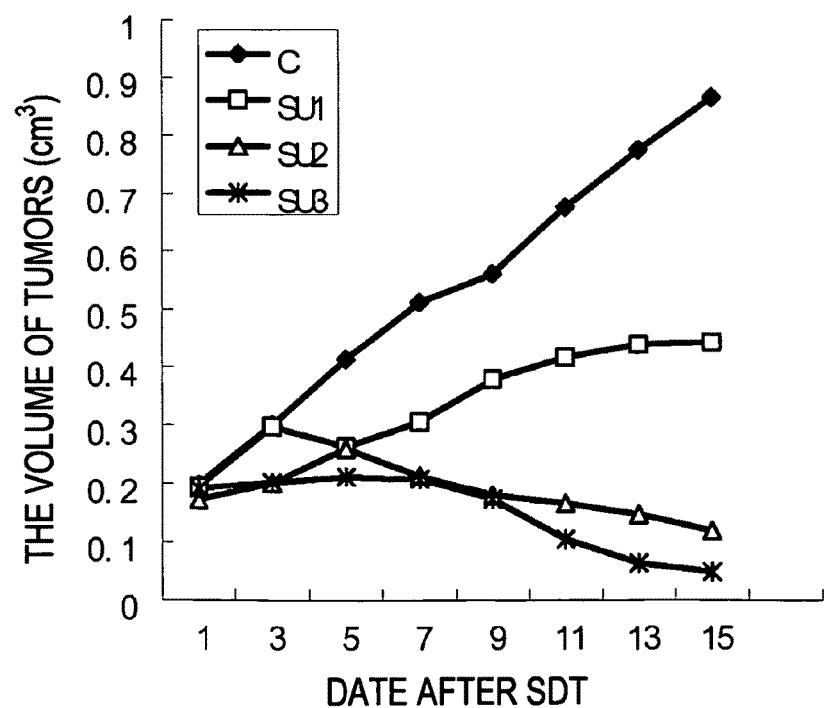
FIG. 4 represents a diagram showing tumor developing profiles observed in three SDT groups administered with the lysine form of tin chlorophyllin, compared to a control group in animal tests.

FIG. 4 and Table 4 show the results of the study on the relationship between the therapeutic effect of SDT and the strength of the power density of ultrasound. As can be seen in FIG. 4, the SDT therapy with the lysine form of tin chlorophyllin exhibited a killing effect on the tumor when ultrasound having a power density in the range of 0.3 W/cm$^2$-1.2 W/cm$^2$ was applied. The therapeutic effect increased proportionally to the increase of the power density.

15 days later, the tumor tissues were excised and weighed (see Table 4). Compared with the control group, the SU1, SU2, and SU3 groups had the significantly decreased average tumor weight with a very significant difference (P<0.05-0.01). Additionally, the SU2 and SU3 groups have the average tumor weights with a very significant difference (P<0.05-0.01) compared with the SU1 group. This demonstrates that the therapeutic effect of the SDT therapy with the lysine form of tin chlorophyllin depends on the strength of the power density of ultrasound, and further confirms that the therapeutic effect of the SDT therapy depends on the synergistic effect of the lysine form of tin chlorophyllin and ultrasound. The SDT therapy with the lysine form of tin chlorophyllin can indeed inhibit the growth of the S-180 tumors in mice.

TABLE 4

Comparison of Tumor Weights between Three SDT Groups Administered with Lysine Form of Tin Chlorophyllin and Control Group

| Group | Average Tumor Weight (g) | P (compared to C) | P (compared to SU1) |
|---|---|---|---|
| C | 0.362 ± 0.096 | | <0.05 |
| SU1 | 0.0435 ± 0.031 | <0.05 | |
| SU2 | 0.022 ± 0.008 | <0.01 | <0.05 |
| SU3 | 0.011 ± 0.004 | <0.01 | <0.01 |

III A Clinical Case

Figure 5:
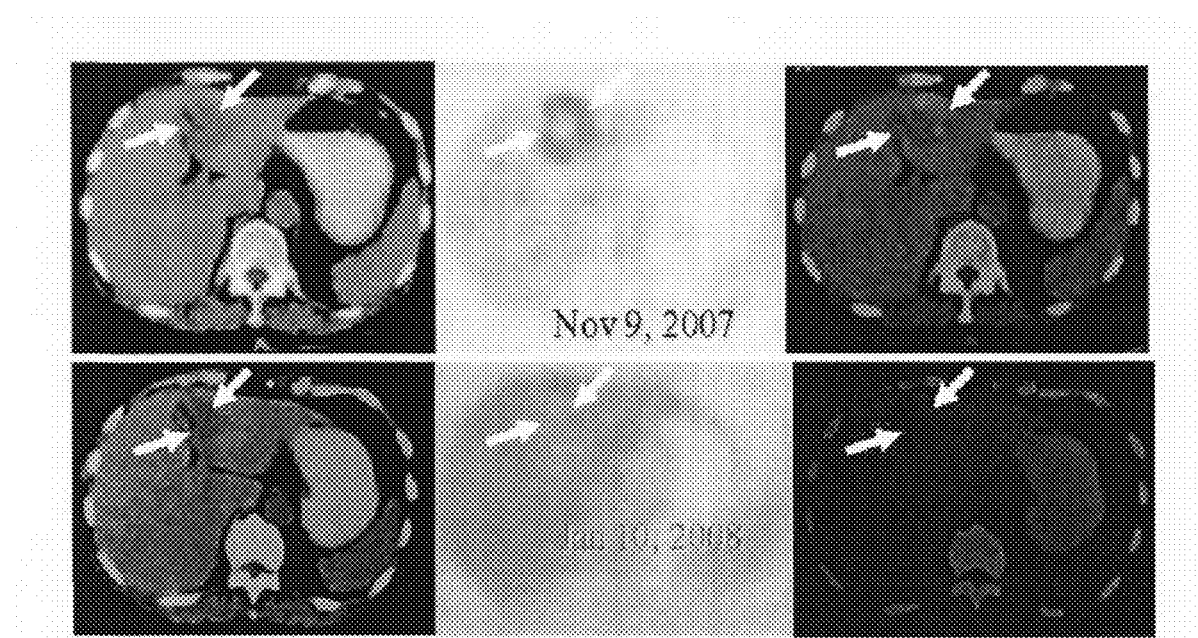
FIG. 5 represents a photograph of PET/CT scan after 3 cycle of SDT treatment with the lysine form of tin chlorophyllin, compared to PET/CT scan before SDT.

A patient, female, 69 years old, with right breast carcinoma. 10 months after surgery and chemotherapy, a tumor metastasis was detected in liver as shows by Computed Tomography-Positron Emission Tomography (CT-PET) on Nov. 9, 2007 (see FIG. 5). The lysine form of tin chlorophyllin as indicated in the above animal test B was dissolved in 0.1 mol/L phosphate buffer (pH 7.4) and given to the patient through lingual absorption every day for 2 days. Total dose of the lysine form of tin chlorophyllin was 60 mg. After 24 h, the red light light-emitting diode (LED) was irradiated to the body surface followed by local ultrasound irradiating of the tumour area at the intensities of 2.0 W/cm$^2$ for 20 minutes in a water bathtub every day for 3 days. One week later, the treatment was repeated. After 3 cycles of SDT treatment with the lysine form of tin chlorophyllin, CT-PET scan on Jan. 10, 2008 showed the tumor shrank and the tumor metabolic activity was inhibited (see FIG. 5). Her symptom was much improved and Blood Routine and chemistry tests showed normal result.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

We claim:
1. A method of sonodynamic therapy for the treatment of sarcomas, comprising administration of dihydroporphin e4 (E4) having the following structural formula to a patient, and applying a sonic wave to the patient,

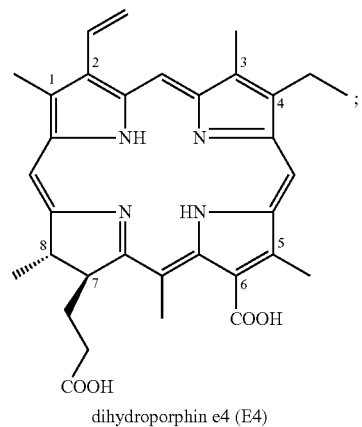

dihydroporphin e4 (E4)

wherein the sonic wave is ultrasound having a frequency in a range of 0.1-10 MHz; and wherein a concentration of the dihydroporphin e4 is 4 mg/mL of water.

2. The method of sonodynamic therapy for the treatment of sarcomas according to claim 1, wherein the sonodynamic therapy comprises applying the sonic wave to the body of the patient topically.

3. The method of sonodynamic therapy for the treatment of sarcomas according to claim 1, wherein the sonodynamic therapy comprises applying the sonic wave to the body of the patient systemically.

4. The method of sonodynamic therapy for the treatment of sarcomas according to claim 1, wherein the ultrasound has an energy density of more than 10 J/cm$^2$.

5. The method of sonodynamic therapy for the treatment of sarcomas according to claim 1, wherein the sonic wave is applied to the patient via a liquid.

6. The method of sonodynamic therapy for the treatment of sarcomas according to claim 1, wherein the sonodynamic therapy comprises applying both the sonic wave and a light wave to the patient, either topically or systemically.

* * * * *